(12) United States Patent
Eriksson et al.

(10) Patent No.: US 7,368,561 B2
(45) Date of Patent: May 6, 2008

(54) ISOLATION OF ANTISENSE OLIGONUCLEOTIDES

(75) Inventors: Kjell Eriksson, Uppsala (SE); Bo-Lennart Johansson, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 316 days.

(21) Appl. No.: 10/535,728

(22) PCT Filed: Nov. 17, 2003

(86) PCT No.: PCT/SE03/01784

§ 371 (c)(1),
(2), (4) Date: May 19, 2005

(87) PCT Pub. No.: WO2004/048569

PCT Pub. Date: Jun. 10, 2004

(65) Prior Publication Data

US 2006/0003331 A1    Jan. 5, 2006

(30) Foreign Application Priority Data

Nov. 28, 2002    (SE) .................................. 0203521

(51) Int. Cl.
*C07H 21/00* (2006.01)
*C07H 21/04* (2006.01)
(52) U.S. Cl. ..................... 536/25.4; 536/24.5
(58) Field of Classification Search .................. None
See application file for complete search history.

(56) References Cited

FOREIGN PATENT DOCUMENTS

| WO | WO 98/00435 | 1/1998 |
|---|---|---|
| WO | WO 99/09045 | 2/1999 |
| WO | WO 02/46398 | 6/2002 |

OTHER PUBLICATIONS

Hubert et al. Journal of Chromatography 1980, vol. 198, pp. 247-255.*
Dobrowolska et al. Journal of Chromatography 1991, vol. 541, pp. 333-339.*
Deshmukh, R., et al., "Process Development for Purification of Therapeutic Antisense Oligonucleotides by Anion-Exchange Chromatography", *Organic Process Research & Development*, vol. 4, No. 3, 2000, p. 205-213.
Deshmukh, R., et al., "Large-scale purification of antisense oligonucleotides by high-performance membrane adsorber chromatography", *Journal of Chromatography A*, vol. 890, 2000, p. 179-192.

* cited by examiner

Primary Examiner—Tracy Vivlemore
(74) Attorney, Agent, or Firm—Yonggang Ji

(57) ABSTRACT

The present invention relates to a method of isolating fully thioated single stranded antisense oligonucleotides from a biological solution, which method comprises the steps of contacting the biological solution with an immobilised metal ion adsorption chromatography (IMAC) resin to adsorb the antisense oligonucleotides to the resin and subsequently contacting the resin with an eluent under conditions that provide desorption of the antisense oligonucleotides from the resin, wherein the fully thioated antisense oligonucleotides are separated from incorrectly thioated antisense oligonucleotides in the solution. The invention also relates to the use of an immobilised metal ion adsorption chromatography (IMAC) resin for isolation of fully thioated single stranded antisense oligonucleotides from a biological solution.

7 Claims, 5 Drawing Sheets

Fully thioated phosphorothioate

Monophosphodiester analog

Single deletion sequence

ISOLATION OF ANTISENSE OLIGONUCLEOTIDES

CROSS REFERENCE TO RELATED APPLICATIONS

This application is a filing under 35 U.S.C. § 371 and claims priority to international patent application number PCT/SE2003/001784 filed Nov. 17, 2003, published on Jun. 10, 2004 as WO 2004/048569 and also claims priority to patent application number 0203521-0 filed in Sweden on Nov. 28, 2002; the disclosures of which are incorporated herein by reference in their entireties.

TECHNICAL FIELD

The present invention relates to a method of isolating antisense oligonucleotides from other components of a biological solution.

BACKGROUND

Biotechnological methods are used to an increasing extent in the production of proteins, peptides, nucleic acids and other biological compounds, for research purposes as well as in order to prepare novel kinds of drugs. Due to its versatility and sensitivity to the compounds, chromatography is often the preferred purification method in this context. The term chromatography embraces a family of closely related separation methods, which are all based on the principle that two mutually immiscible phases are brought into contact. More specifically, the target compound is introduced into a mobile phase, which is contacted with a stationary phase. The target compound will then undergo a series of interactions between the stationary and mobile phases as it is being carried through the system by the mobile phase. The interactions exploit differences in the physical or chemical properties of the components in the sample.

Interactions between a target compound and metal chelating groups present on the stationary phase are utilised in a chromatographic purification method denoted immobilised metal ion adsorption chromatography (IMAC), also known as metal chelating affinity chromatography (MCAC), which is often used for the purification of proteins. The principle behind IMAC lies in the fact that many transition metal ions can coordinate to phosphate groups and nitrogen atoms, such as in the amino acids histidine, cystein, and tryptophan, via electron donor groups on the amino acid side chains. To utilise this interaction for chromatographic purposes, the metal ion must be immobilised onto an insoluble support. This can be done by attaching a chelating group to the chromatographic matrix. Most importantly, to be useful, the metal of choice must have a higher affinity for the matrix than for the compounds to be purified. Examples of suitable coordinating ions are Cu(II), Zn(II), Ni(II), Ca(II), Co(II), Mg(II), Fe(III), Al(III), Ga(III), Sc(III) etc.

Various chelating groups are known for use in IMAC, such as iminodiacetic acid (IDA), which is a tridentate chelator, and nitrilotriacetic acid (NTA), which is a tetradentate chelator. Elution of an IMAC resin is as regards proteins commonly performed by addition of imidazol. Alternatively, elution is conventionally performed by lowering the pH.

In recent years, IMAC has successfully been used for the purification of proteins and peptides, wherein His-tags have been introduced by recombinant techniques to facilitate efficient purification thereof by IMAC. For this reason, IMAC has assumed a more important role in large-scale protein and/or peptide production. In addition, IMAC has also been used in purification of phosphorylated proteins and peptides from tryptic protein digests. Such phosphorylated proteins and peptides can subsequently be analysed by ESI/MS/MS to determine the phosphorylated sites therein.

Further, during the period when the IMAC was relatively new, use thereof for purification of various compounds were suggested. For example, Porath et al (U.S. Pat. No. 4,677, 027) disclosed in 1985 how biological macromolecules and particles can be separated using a product consisting of a solid phase having immobilised metal ions on its surface substituted via a metal chelate bond with a polymer. The envisaged biomolecules are virus and cells, but polysaccharides, proteins and also oligonucleotides are mentioned. However, since then, oligonucleotides have due to more recent scientific findings found new applications, in turn necessitating novel modifications thereof.

One example of a more recently developed field, wherein oligonucleotides are modified, is the antisense technology in drug discovery. Antisense drugs work at the genetic level to interrupt the process by which disease-causing proteins are produced. This is possible, since proteins have been shown to play a central role in virtually every aspect of human metabolism. Almost all human diseases are the result of inappropriate protein production, or a disordered protein performance. This is true of both host diseases, such as cancer, and infectious diseases, such as AIDS. Traditional drugs are designed to interact throughout the body with protein molecules that support or cause diseases. Antisense drugs are designed to inhibit the production of disease-causing proteins. They can be designed to treat a wide range of diseases including infectious, inflammatory and cardiovascular diseases and cancer and have the potential to be more selective, and, as a result, more effective and less toxic than traditional drugs. The mechanisms behind antisense technology have been widely described, see e.g. Uhlmann et al in Antisense Oligonucleotides: A New Therapeutic Principle, Chemical Reviews, Vol. 90, Number 4, June 1990. In brief, as is well known, during transcription of DNA into RNA, the two complementary strands of the DNA partly uncoil, whereby the strand known as the sense strand separates from the strand known as the antisense strand. The antisense strand is then used as a template for transcribing enzymes that assemble mRNA in the process known as transcription. The mRNA then migrates into the cell, where ribosomes read the encoded information and string together amino acids to form a specific protein in the process known as translation. Now, the antisense drugs are complementary strands of small segments of mRNA, and they can be either DNA or RNA. To create antisense drugs, nucleotides are linked together in short chains known as oligonucleotides. Each antisense drug is designed to bind a specific sequence of nucleotides in its mRNA target to inhibit production of protein encoded by the target mRNA.

The linking together of oligonucleotides can be performed in any kind of commercially available automated solid-phase synthesiser for synthesis of oligonucleotides under cGMP conditions for clinical studies and commercial drug supplies.) In such synthesis, the oligonucleotides, wherein one oxygen atom of the phosphate group of each base in the native nucleic acid has been exchanged for a sulphur atom, are easily produced. However, an inherent problem in the synthesis of such thioated oligonucleotides, herein-denoted antisense oligonucleotides, is the fact that it will be practically impossible to perform with a yield of 100% correctly phosphorothioated oligonucleotides. Instead, a yield in the range of about 70-75% is usually obtained. Accordingly, before any antisense drug can be prepared thereof, the synthesised product will require a subsequent purification in order ensure a sufficient quality.

Reverse phase HPLC is commonly used for purification of antisense oligonucleotides. However, use of high pressures is in general not considered to be advantageous conditions for this kind of process, since it put high demands on the equipment used and also makes the process difficult, and consequently costly, to scale-up. In addition, the organic solvents commonly used in this technology may be undesirable for some applications.

Deshmukh et al (Deshmukh, R. R., Miller, J. E., De Leon, P., Leitch, W. E., Cole, D. L., and Sanghvi, Y. S. in "Process Development for Purification of Therapeutic Antisense Oligonucleotides by Anion-Exchange Chromatography", Organic Process Research & Development 2000, 4, 205-213) describes the development of an anion-exchange chromatography method for purification of phosphorothioate antisense oligonucleotides. More specifically, 20-mers which are antisense inhibitors of the cell adhesion molecule ICAM-1 were synthesised and subsequently purified on an anion exchanger carrying quaternary arnmonium functional groups on a polystyrene-based matrix (Source 15 and Source Q 30, both from Amersham Biosciences AB, Uppsala, Sweden). The most advantageous resolution is observed for the higher pH value tested for elution, which was pH 11. However, it has still to be shown whether or not a fully thioated 20-mer can be separated from a 20-mer, wherein one or more of the target oxygens have not been substituted with sulphurs. Thus, the selectivity obtainable with ion exchange for purification of antisense oligonucleotides is still not fully satisfactory. In addition, another disadvantage is that such purification of antisense oligonucleotides by anion-exchange chromatography will also require a step of desalting afterwards, which involves a further process step and consequently a higher process cost in total.

Similarly, Deshmukh et al (Deshmukh, R. R., Warner, T. N., Hutchison, F., Murphy, M., Leitch, W. E., De Leon, P., Srivatsa, G. S., Cole, D. L., and Sanghvi, Y. S. in "Large-scale purification of antisense oligonucleotides by high-performance membrane adsorber chromatography", Journal of Chromatography A, 890 (2000) 179-192) have suggested purification of antisense oligonucleotides using strong anion exchange membranes. However, like in the above described method, the selectivity obtainable is still not fully satisfactory (is this true, can we add any other disadvantages/ differences). In addition, use of membranes entails a low capacity and hence large size membranes will be required for a reasonably efficient process. Finally, this method will like the above-discussed anion-exchange also require a step of desalting afterwards.

WO 99/09045 (Somagenics, Inc.) relates to antisense and antigene therapeutics with improved binding properties and methods for their use. More specifically, the invention relates to antisense and antigene oligonucleotides capable of topologically linking to target nucleic acid in a manner that improves translation and transcription inhibitory properties. In one embodiment, phosphorothioate analogues of nucleic acids are disclosed, which have sulphur in place of non-bridging oxygens bonded to phosphorous in terminal or internucleotide phosphates. This modification is allegedly capable of a stronger binding to metallo-affinity chromatography media than the unmodified equivalents. However, there is no suggestion or guidance that metallo-affinity chromatography could be useful to separate oligonucleotides having a varying degree of thioation. Further, in another embodiment, the oligonucleotides have been platinated. Such platinated oligonucleotides are easily separated from reaction mixtures by preparative electrophoresis, or alternatively by ion-exchange column chromatography. It is also suggested to use metallo-affinity chromatography on mercurated columns as a one-step method of purification of platinated oligonucleotides, but this is a mere suggestion. Nothing in this document provides any evidence that such purification would be efficient or even work, and the components of said "reaction mixture" are not defined.

Thus, there is still a need of alternative procedures for the purification of antisense oligonucleotides, especially of methods sensitive enough to separate antisense oligonucleotides of different thioation degree from each other.

SUMMARY OF THE PRESENT INVENTION

One object of the present invention is to provide a method of isolating antisense oligonucleotides from corresponding incorrectly synthesised oligonucleotides and/or not fully thioated oligonucleotides in a biological solution. This can be achieved by the method as defined in the claims.

A specific object of the invention is to provide a method of isolating antisense oligonucleotides from a biological solution, which method exhibits an improved selectivity as compared to the prior art methods.

Another object of the invention is to provide a method of isolating antisense oligonucleotides from a biological solution, which method reduces the need of organic solvents and/or high pressures as compared to prior art methods.

A further object of the present invention is to provide a method of isolating antisense oligonucleotides from a biological solution, which method is easy to scale up and hence more cost-effective than the prior art methods.

Other objects and advantages of the present invention will appear from the detailed disclosure that follows.

DEFINITION

Figure 1:
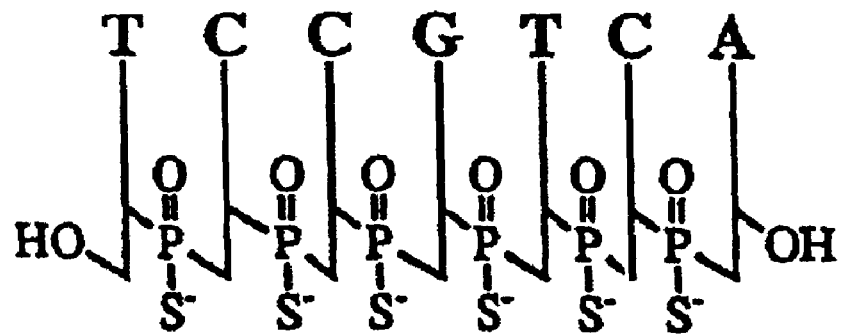
FIG. 1 shows an example of a seven-base full-length, fully thioated phosphorothioate (a); its monophosphodiester analogue (b) and a single deletion sequence (c).
Figure 1:
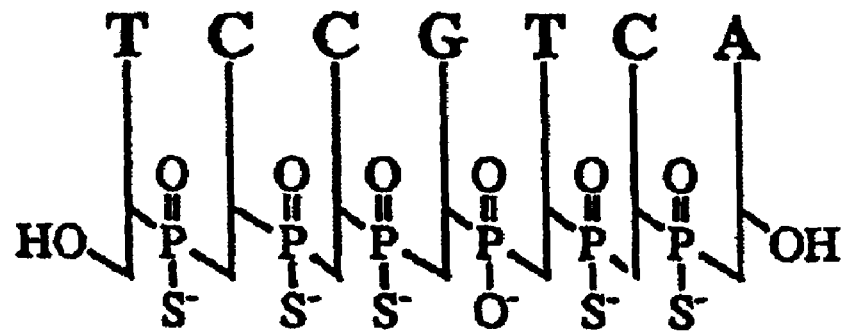
Figure 1:
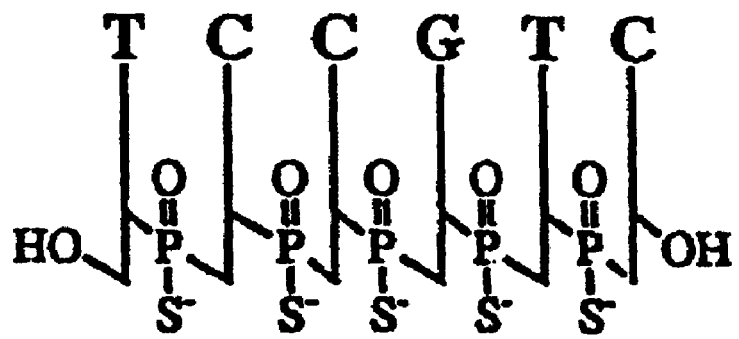

In this specification, the term "oligonucleotide" is used in its conventional meaning, i.e. to mean a sequence of nucleotides, and the term "polynucleotide" refers to a longer sequence of nucleotides than the oligonucleotide.

The term a "nucleotide" means a residue comprised of three parts, namely an inorganic phosphate, a simple sugar and either a purine or a pyrimidine base. In each nucleotide, the three parts are attached to each other in the order-phosphate-sugar-base-. In an oligonucleotide, ester bonds link the sugar and phosphate components of adjacent nucleotide monomers. Since the sugar and the phosphate within a nucleotide monomer are also linked via an ester bond, the sugar-phosphate-sugar linkage along the backbone of a poly- or oligonucleotide chain is known as a phosphodiester bond.

The term "chromatography" encompasses chromatographic separation methods performed in packed columns, in expanded or suspended beds and on membranes.

The term "resin" refers to the solid phase used in chromatography, i.e. the adsorbent that captures the target species. A "resin" may be produced in the form of porous or non-porous spherical or essentially spherical particles, beads, such as beads for expanded bed adsorption, and monoliths. Further, by providing the resin on a support, membranes can be provided, which are also useful for isolation of a species from a liquid. A resin is also known in this field as a matrix.

The term "adsorption" means herein the binding of a species to a ligand on a resin.

The term "eluent" is used herein in its conventional meaning i.e. for a solution capable of perturbing the interaction between the solid phase (resin) and product (target species) and promoting selective dissociation of the product from the solid phase.

Consequently, the term "desorption" means to perturb the interaction as explained above.

The term "buffer" or "buffered solution" refers to a mixture of acid and base which when present in a solution reduces or modulates changes in pH that would otherwise occur in the solution when acid or based is added.

The term "isolation" means herein a separation from other components and provides a substantially pure target compound, such as a substantially pure antisense oligonucleotide.

DETAILED DESCRIPTION OF THE INVENTION

A first aspect of the present invention is a method of isolating fully thioated single stranded antisense oligonucleotides from a biological solution, comprising the steps of contacting the biological solution with an immobilised metal ion adsorption chromatography (IMAC) resin to adsorb the antisense oligonucleotides to said resin and subsequently contacting the resin with an eluent under conditions that provide desorption of the antisense oligonucleotides from said resin, wherein the fully thioated antisense oligonucleotides are separated from incorrectly thioated antisense oligonucleotides in said solution. Thus, the present invention enables to purify the fully thioated single stranded antisense oligonucleotides other components of a biological solution, and hence allows to obtain said oligonucleotides in a substantially pure form.

As is well known to those of skill in this field, during the synthesis of antisense oligonucleotides, besides oligonucleotides of an incorrect length, the most prevalent contamination is oligonucleotides that have not been fully thioated. Accordingly, the present invention fulfils an important need in the production of antisense oligonucleotides for therapeutical or other applications.

Thus, the present invention utilises for the first time to our knowledge the interaction of a metal with the backbone phosphothioate group of a nucleic acid in the purification of antisense oligonucleotides. Without wishing to limit the present invention to any specific interactions, it is also assumed that the nitrogen atoms of one or more of the bases adenine, guanine, uracil, cytosine and thymine of the oligonucleotide may also be involved in this binding.

In the present context, it is to be understood that the term "fully" thioated means that in 100% of the phosphate backbone groups present in a corresponding native oligonucleotide, one of the non-bridging oxygen atoms in the phosphate backbone has been replaced by a sulphur atom.

The IMAC resin used in the present method can be any resin, such as the once exemplified in the section "Background". In brief, metal chelating groups include for example the iminodiacetic (IDA) group, the tris(carboxymethyl)-ethylenediamine (TED) group, the N-(hydroxyethyl) ethylenediaminetriacetic group, and derivatives such as the N-(methyl), and the N-(hydroxymethyl) IDA groups. These groups can be cross-linked to the natural or synthetic polymeric support by standard aliphatic ether linkages and reagents, such as bisoxirane, epichlorhydrin, and 1,4-bis-(2,3-epoxypropoxy)butane. Examples of natural polymeric support materials are e.g. agarose, alginate, carrageenan, gelatin etc. Synthetic polymers can be illustrated by styrene or derivatives, divinylbenzene, acrylamide, acrylate esters, methacrylate esters, vinyl esters, vinyl amides etc, optionally cross-linked with any conventional cross-linker, such as divinylbenzene, di- or polyfunctional (meth)acrylate esters, di- or polyfunctional (meth)acrylamides, triallylisocyanurate, divinylamides. For clarity, in this context, it is understood that an IMAC resin as used in the present method is comprised of a support to which chelating groups have been attached, and charged with coordinating ions. Examples of suitable coordinating metal ions are e.g. Al, Ce, Cu, Co, Fe, In, Ga, Ge, Lu, Ni, Ru, Sb, Sc, Sn, Yc, Zn, Zr, Ta and Th ions. In one embodiment of the present invention, the metal ion is $Zr^{2+}$ or $Fe^{3+}$. According to the present invention, this embodiment provides a stronger bond to the phosphor of the bridge than to the corresponding sulphur. IMAC resins are also commercially available, such as HiTrap™ Chelating HP Columns and Chelating Sepharose™ Fast Flow, both from Amersham Biosciences AB, Uppsala, Sweden.

In this context, it is understood that the term "resin" is used to encompass particles and beads as well as monoliths and membranes.

The desired antisense oligonucleotides can be separated from many kinds of components of the biological solution, such as proteins or incorrectly synthesised oligonucleotides, in large depending on the nature of the biological solution. Thus, in one embodiment, the biological solution is provided from an automated synthesis of antisense oligonucleotides. Hence, in this embodiment, the biological solution is a synthesis solution. In a similar embodiment, the biological solution is a solution wherein the antisense oligonucleotides have been synthesised using non-automated methods. Thus, synthesis can be performed in solution according to well-known methods or in any commercially available kind of equipment, such as a ÄKTA™ oligopilot (Amersham Biosciences AB, Uppsala, Sweden). In another embodiment, the biological solution is serum, such as human serum, and the purpose of the method can then be to quantify the antisense oligonucleotides present therein. This embodiment can be part of treatment scheme, wherein it is desired to test the presence of drug i.e. antisense oligonucleotide in the blood of the patient.

In one embodiment, the isolated single stranded (ss) antisense oligonucleotides are of a size in the range of 10-30 bases, such as 15-25 bases and more specifically 18-21 bases. In a specific embodiment, the antisense oligonucleotides are of a size in the range of about 18-20 bases. In another embodiment, the antisense oligonucleotides are comprised of up to about 25 bases, such as up to 20 bases. In yet another embodiment, the antisense oligonucleotides are comprised of at least 5 bases, such as at least about 10 bases. However, in this context, since it is well-known that the kind of condition to be treated using the antisense technology will decide the nature, such as the base sequence and the size, of the antisense oligonucleotide, it is understood that the present invention also encompasses shorter or longer oligonucleotides as well, if they are useful in an antisense technology-based drug. Such drugs are useful in the treatment of both host diseases, such as cancer, and infectious diseases, as discussed in further detail in the section "Background" above.

However, as also indicated in the background section above, the synthesis of antisense oligonucleotides often results in part in incorrectly synthesised antisense oligonucleotides. The most common impurities in a biological solution that results from such synthesis are deletion sequences, i.e. antisense oligonucleotides which are one or more bases shorter than the desired product. Such deleted oligonucleotides can be described as (n-1) mers, (n-2) mers, (n-3) mers etc, wherein n denotes the number of nucleotides of the desired full-length product. Thus, in one embodiment of the present method, the fully thioated antisense oligonucleotides are separated from incorrectly synthesised oligonucleotides. Other examples of incorrectly synthesised oligonucleotides are addition sequences, i.e. antisense oligonucleotides that are longer than the desired products, and branched products.

Another example of undesired components in a biological solution resulting from antisense oligonucleotide synthesis is incorrectly thioated sequence, i.e. not fully thioated oligonucleotides. As mentioned above, these are one of the most commonly occurring contaminations in a synthesis solution. The most prevalent form is oligonucleotides with one or two bonds without thioation. Thus, in one embodiment of the present method, fully thioated antisense oligonucleotides are separated from incorrectly thioated antisense oligonucleotides containing 1 to 5, such as 1 or 2, bonds without thioation. Further examples of incorrectly thioated oligonucleotides are for example 20-meric oligonucleotides wherein one phosphodiester group has not been correctly thioated, and hence oligonucleotide which are about 95% thioated are separated from the fully thioated ones. Similarly, a 19-meric, 18-meric or 17-meric oligonucleotide wherein one base has not been correctly thioated is thioated to about 94%. Accordingly, in one embodiment, the present fully thioated antisense oligonucleotides are isolated from oligonucleotides that are thioated to about 90%, such as about 94%, and preferably to about 95%. In another embodiment, the present fully thioated antisense oligonucleotides are isolated from oligonucleotides that are thioated to about 40%, preferably to about 60%, more preferably to about 80% and most preferably to about 90%.

In the prior art, when proteins and/or peptides have been isolated using IMAC, conditions of neutral or close to neutral pH, such as about 7.5-8.0, have been utilised. The present inventors unexpectedly found that when antisense oligonucleotides are isolated using IMAC, a lower pH is more favourable. Thus, in one embodiment of the present method, the conditions for adsorption are defined by a pH value below neutral. In a specific embodiment, the pH is adapted to below about 7, such as about 5. Thus, the pH of the biological solution at the contact with the resin may be in a range of 0-7, 0-6 or 0-5. The pH is easily adjusted by the skilled person in this field by adding a suitable buffer or acid, such as dilute acetic acid. In an advantageous embodiment, the pH is adjusted to about 5.0 and the buffer used is 15 mM sodium acetate. As is easily realised, since oligonucleotides are sensitive to extreme pH values, care should be taken not to adjust the pH in any way that can harm the antisense oligonucleotides.

The elution of the desired antisense oligonucleotides from the resin can be performed according to standard methods using an increasing pH and/or phosphate gradient, for example using potassium phosphate. An illustrative gradient is as used in the experimental part below, namely starting from the pH used for adsorption, such as from 0.1% acetic acid to 0.5 M potassium phosphate. In an alternative embodiment, the gradient is from pH 3.0 to 0.2 M potassium phosphate. Other well-known salts and buffers are also useful for the elution, and the skilled person can easily set the appropriate conditions for elution. As the skilled person in this field will realise, the addition of salt will increase the ionic strength, and hence the pH surrounding the antisense oligonucleotides will change slightly. However, the pH in general during the adsorption of the antisense oligonucleotides will still be lower than the conditions known for use of IMAC for protein separation.

In a specific embodiment, the present method in addition comprises a subsequent step of polishing the isolated antisense oligonucleotides. Such polishing is easily performed by the skilled person in this field, such as by gel filtration, detritylation precipitation, desalting, change of buffer etc.

Even though the examples shown below utilises a small lab scale, it is understood that the skilled person in this field can easily scale up the present method to s size useful in a production plant. Thus, one advantage with the present method is that it requires less expensive solvents and equipment than e.g. the previously suggested reverse phase chromatography (RPC) method.

A second aspect of the present invention is an antisense oligonucleotide isolated by a method as defined above. Thus, the fully thioated single stranded antisense oligonucleotides according to the invention are obtained in a purity of at least about 80%, more preferably at least about 90% and most preferably at least about 95%, such as close to 100%.

A third aspect of the present invention is the use of an immobilised metal affinity chromatography (IMAC) resin for isolation of antisense oligonucleotides from corresponding oligonucleotides in a biological solution. The IMAC resin can be as discussed in relation to the method according to the invention, and the considerations discussed above may also apply to the present use.

Finally, the present invention also relates to a kit for purification of fully thioated single stranded antisense oligonucleotides from a biological solution, which kit comprises a chromatography column packed with an immobilised metal ion adsorption chromatography (IMAC) resin and written instructions for separation of said fully thioated oligonucleotides from not fully thioated oligonucleotides. The present kit may comprise a column of laboratory scale or a column of a size suitable for large-scale production of antisense oligonucleotides. Further, the kit may comprise buffer(s) suitable for elution and optionally also for washing in a separate compartment(s).

DETAILED DESCRIPTION OF THE DRAWINGS

FIG. 1 shows an example of a seven-base full-length, fully thioated phosphorothioate (a); its monophosphodiester analogue (b) and a single deletion sequence resulting in a (n−1) mer (c).

Figure 2:
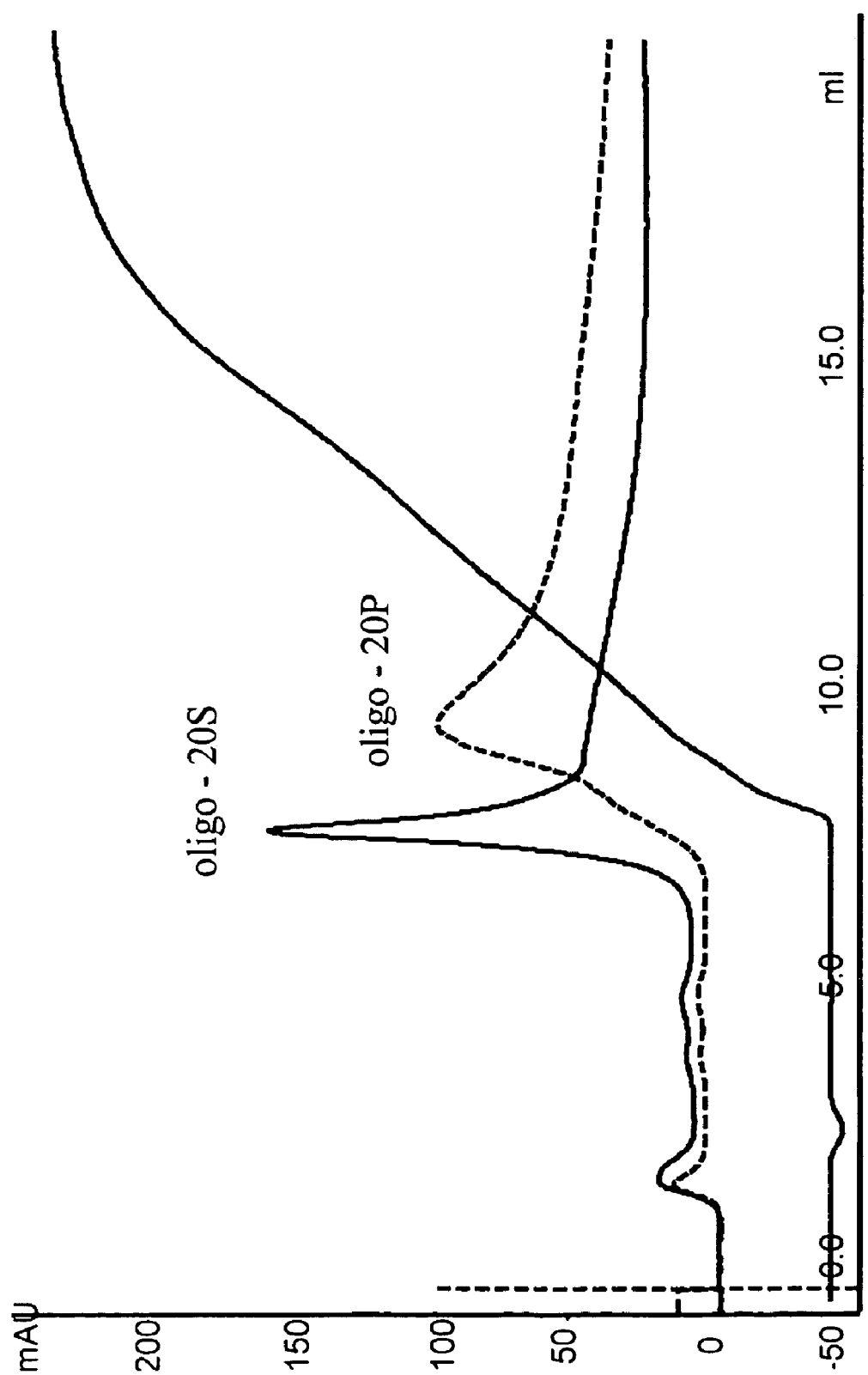
FIG. 2 shows IMAC using $Fe^{3+}$ as metal ion as described in Example 1 below and illustrates a comparison of elution of two different oligonucleotides with the same sequence of bases.

FIG. 2 shows IMAC using $Fe^{3+}$ as metal ion as described in Example 1 below and illustrates a comparison of elution of two different oligonucleotides with the same sequence of bases. The X-axis shows the retention volume in ml, while the Y-axis shows the UV absorbance at 260 nm in mAU. One of the oligonucleotides is fully thioated (denoted 20S in FIG. 2), while the other one is unmodified (denoted 20P in FIG. 2). It appears clearly that the antisense oligonucleotide can be separated from the phosphodiester (non-modified) form of oligonucleotides, the thioated form being eluted as a relatively narrow peak at 7.3 ml, before the unmodified form. The two small peaks eluted early in the chromatogram are presumably synthesis-related, and are caused by impurities in the sample that do not contain any phosphotioates or phosphodiester groups.

Figure 3:
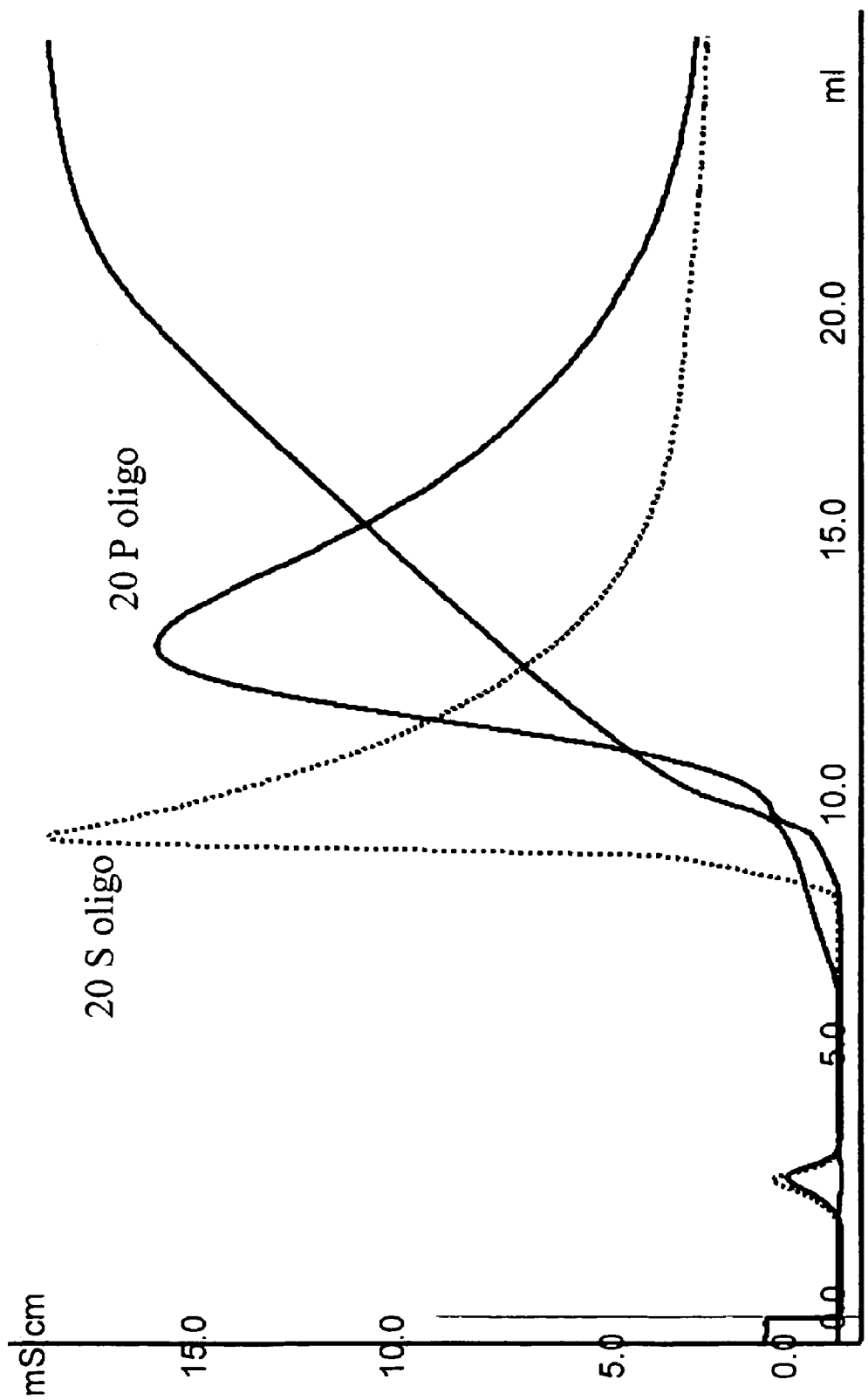
FIG. 3 shows IMAC using $Zr^{2+}$ as metal ion as described in Example 2 below and illustrates a comparison of elution of two different oligonucleotides with the same sequence of bases.

FIG. 3 shows IMAC using $Zr^{2+}$ as metal ion as described in Example 2 below and illustrates a comparison of elution of two different oligonucleotides with the same sequence of bases. X- and Y-axis are as described above. One of the oligonucleotides is fully thioated (denoted 20S in FIG. 3), while the other one is unmodified (denoted 20P in FIG. 3). It appears clearly that the antisense oligonucleotide can be separated from the phosphodiester (non-modified) form of oligonucleotides, the thioated form again being eluted as a relatively narrow peak at about 9.4 ml, before the unmodified form. The two small peaks eluted early in the chromatogram are explained as above for FIG. 2. A comparison of FIG. 2 and FIG. 3 reveals a stronger affinity of the oligonucleotides for the Zr-ion than the Fe-ion, however it is noted that the conditions used have not been optimised.

Figure 4:
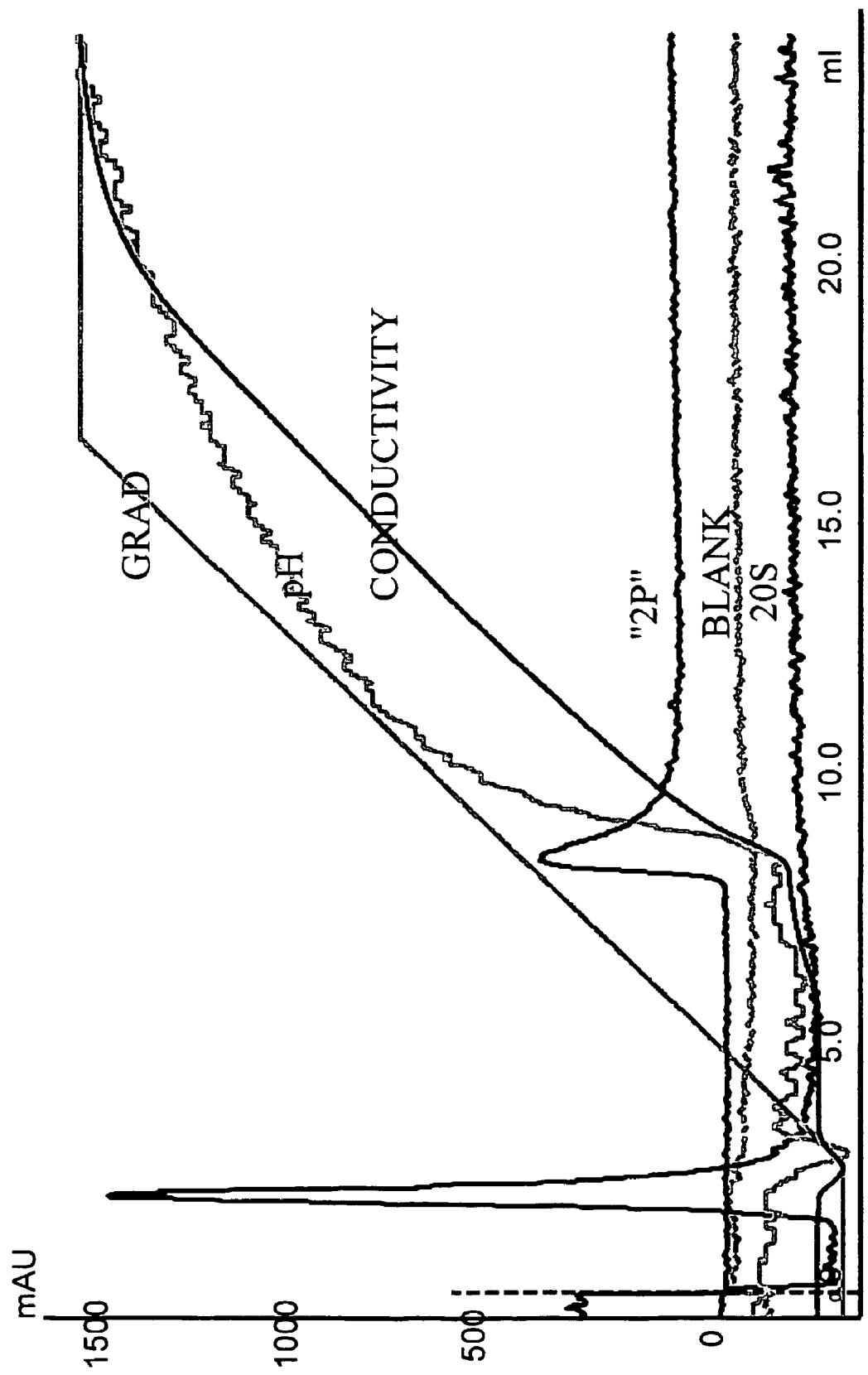
FIG. 4 shows an example of an efficient separation of a fully thioated (20S) oligonucleotide from an oligonucleotide with two phosphodiester bonds ("2P") using IMAC.

FIG. 4 shows an example of an efficient separation of two oligonucleotides having the same sequence, as described in detail in example 3. More specifically, this drawing shows that it is quite possible to separate a fully thioated (20S) oligonucleotide from an oligonucleotide with two phosphodiester bonds ("2P") using IMAC. The peaks are clearly separated in the chromatogram. For elution, a 10 CV linear gradient from 15 mM sodium acetate to 0.2 M potassium phosphate was used.

Figure 5:
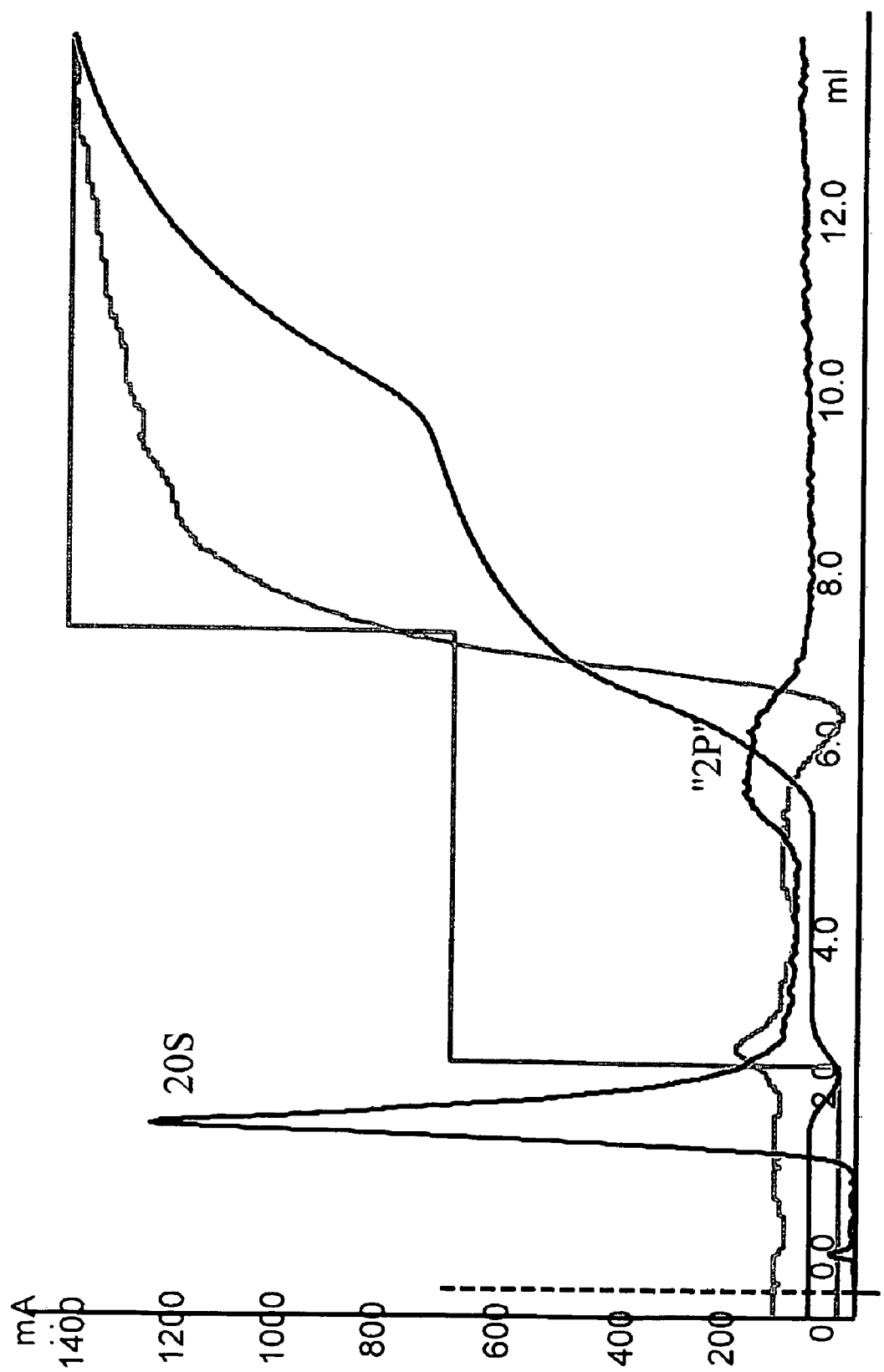
FIG. 5 shows a clear separation of a fully thioated (20S) oligonucleotide from an oligonucleotide with two phosphodiester bonds ("2P") using IMAC, this time by step-wise elution.

FIG. 5 shows again a clear separation of two oligonucleotides having the same sequence as described in example 4. More specifically, this drawing shows a complete, baseline resolution of the peaks corresponding to a fully thioated oligonucleotide (20S) from that of an oligonucleotide with two phosphodiester bonds ("2P"). Thus, the present invention shows that it is possible to separate a fully thioated oligonucleotide from an oligonucleotide with two phosphodiester bonds using IMAC and step-wise elution. For elution, a step gradient was used: Step 1 was at 0.1 M potassium phosphate and step two at 0.2 M potassium phosphate. The results obtained in examples 3 and 4 as illustrated in FIGS. 4 and 5 provide evidence that supports an essential importance of the phosphonate groups in the present binding, not the bases. Thus, this contradicts what was indicated in the above discussed WO 99/09045, where it was stated that a higher degree of thioation would yield a stronger binding to an IMAC resin.

EXPERIMENTAL PART

The present examples are provided for illustrative purposes only and should not be construed as limiting the scope of the present invention as defined by the appended claims. All references given below and elsewhere in the present specification are hereby included herein by reference.

Example 1

Purification of Single Stranded Antisense Oligonucleotides by IMAC Using $Fe^{3+}$ as Metal Ion The oligonucleotides used in this study were 20-mers with the sequence GCC CAA GCT GGC ATC CGT CA (SEQ ID NO:1). Two different oligonucleotide were used, one fully thioated and one without any modification (phosphodiester form).

For the study was used a small IMAC column with IDA chemistry, the HITRAP™ Chelating HP column (1 ml volume) (available from Amersham Biosciences AB, Uppsala, Sweden, Prod # 17-0408-01).

The solvents/buffer used in this example are for IMAC rather unusual. As binding "buffer" a solution of 0.1% acetic acid in water was used. The elution was achieved with a 10 Column Volume linear gradient from 0.1% acetic acid in water to 0.05 M potassium phosphate. However, it is noted that these conditions were not optimised, neither for binding (adsorption) nor for elution.

Flow rate of the eluent was 1 ml/min and detection was made with UV at 260 nm.

Thus, the $Fe^{3+}$ was tested and found useful as a metal ion in the method according to the invention. The results of this example are as shown in FIG. 2.

Example 2

Purification of Single Stranded Antisense Oligonucleotides by IMAC Using $Zr^{2+}$ as Metal Ion The oligonucleotides used in this study were the 20-mers described in Example 1 above.

For the study was used a small IMAC column with IDA chemistry, the HITRAP™ Chelating HP column (1 ml volume) (available from Amersham Biosciences AB, Uppsala, Sweden, Prod # 17-0408-01).

In this example, the binding "buffer" was like in Example 1 a solution of 0.1% acetic acid in water. The elution was achieved herein with a 10 Column Volume linear gradient from 0.1% acetic acid in water to 0.2 M potassium phosphate. However, it is noted that these conditions were not optimised either.

Flow rate of the eluent was 1 ml/min and detection was made with UV at 260 nm.

Thus, $Zr^{2+}$ was tested and found useful as a metal ion in the method according to the invention. The results of this example are shown in FIG. 3.

Example 3

Purification of Synthetic (Antisense) Oligonucleotides from Not Fully Thioated Oligonucleotides by IMAC, Elution by Linear Gradient This example shows the method according to the present invention is capable of separating fully thioated oligonucleotides from just partly thioated oligonucleotides.

The oligonucleotides used in this study were 20-mers with the sequence GCC CAA GCT GGC ATC CGT CA (SEQ ID NO:1). Two different oligonucleotides were used, one fully thioated and one with two of the bonds without modification (phosphodiester form). The phosphodiester bonds were at position 10 and 15 (defined from the 5' end), respectively.

For the study was used a small IMAC column with IDA chemistry, the HITRAP™ Chelating HP column (1 ml volume) (Amersham Biosciences, Uppsala, Sweden, Prod # 17-0408-01). $Zr^{2+}$ was the metal ion studied.

The solvents and buffers used herein are for IMAC rather unusual. As binding buffer, 15 mM sodium acetate and pH is 5.0 was used. The elution was achieved by potassium phosphate, 0.2 M, pH 6.5. The flow rate was 1 ml/min and detection was made with UV at 260 nm.

The results are shown in FIG. 4, which also provides a comparison between the fully thioated (20S) and the oligonucleotide with two phosphodiester bonds ("2P").

Example 4

Purification of Synthetic (Antisense) Oligonucleotides from Not Fully Thioated Oligonucleotides by IMAC, Elution by Step Gradient This is a second example that illustrates how the method according to the present invention is capable of separating fully thioated oligonucleotides from partly thioated oligonucleotides. The starting materials and instruments were as in Example 3 above, the buffer is 15 mM sodium acetate, pH 5.0, and in this example the elution is made by a step gradient. The first step is 2 CV at 0.1 M potassium phosphate and the second step is with 2 CV at 0.2 M potassium phosphate. The results are provided in FIG. 5, which shows a separation of a mixture of two oligonucleotides, a fully thioated (20S) and an oligonucleotide with two phosphodiester bonds ("2P").

What is claimed is:

1. A method of isolating fully thioated single stranded antisense oligonucleotides from a biological solution, which method comprises the steps of contacting the biological solution with an immobilised metal ion adsorption chromatography (IMAC) resin to adsorb antisense oligonucleotides to said resin and subsequently contacting the resin with an eluent under conditions that provide desorption of the antisense oligonucleotides from said resin, wherein the fully thioated antisense oligonucleotides are separated from incorrectly synthesised and/or incorrectly thioated antisense oligonucleotides in said solution; further wherein the metal ion is $Zr^{2+}$ or $Fe^{3+}$.

2. The method of claim 1, wherein the biological solution is a synthesis reaction of antisense oligonucleotides.

3. The method of claim 1, further wherein fully thioated antisense oligonucleotides are separated from incorrectly synthesised oligonucleotides.

4. The method of claim 1, wherein fully thioated antisense oligonucleotides are separated from incorrectly thioated antisense oligonucleotides containing 1-5 bonds without thioation.

5. The method of claim 1, wherein the antisense oligonucleotides are of a size in the range of 5-30 base pairs.

6. The method of claim 1, wherein the pH of the biological solution is below about 7 during the adsorption of antisense oligonucleotides.

7. The method of claim 1, which in addition comprises a subsequent step of polishing the isolated antisense oligonucleotides.

* * * * *

SEQUENCE LISTING

<160> NUMBER OF SEQ ID NOS: 1

<210> SEQ ID NO 1
<211> LENGTH: 20
<212> TYPE: DNA
<213> ORGANISM: Artificial Sequence
<220> FEATURE:

-continued

```
<223> OTHER INFORMATION: Synthetic Oligonucleotide

<400> SEQUENCE: 1
gcccaagctg gcatccgtca                                              20
```